(12) United States Patent
Li et al.

(10) Patent No.: US 8,694,093 B2
(45) Date of Patent: Apr. 8, 2014

(54) METHOD AND APPARATUS FOR RECOGNIZING SENSED CARDIAC EVENTS USING DIFFERENT ELECTRODE CONFIGURATIONS

(71) Applicant: Cardiac Pacemakers, Inc., St. Paul, MN (US)

(72) Inventors: Dan Li, Shoreview, MN (US); Shibaji Shome, Arden Hills, MN (US); Yinghong Yu, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/783,658

(22) Filed: Mar. 4, 2013

(65) Prior Publication Data

US 2013/0253350 A1    Sep. 26, 2013

Related U.S. Application Data

(60) Provisional application No. 61/615,444, filed on Mar. 26, 2012.

(51) Int. Cl.
*A61N 1/00* (2006.01)
*A61B 5/04* (2006.01)

(52) U.S. Cl.
USPC .............................................. 607/2; 600/509

(58) Field of Classification Search
None
See application file for complete search history.

(56) References Cited

U.S. PATENT DOCUMENTS

| | | | |
|---|---|---|---|
| 5,645,070 A * | 7/1997 | Turcott ........................ 600/515 |
| 6,351,673 B1 | 2/2002 | Ding et al. |
| 7,158,830 B2 | 1/2007 | Yu et al. |
| 7,376,458 B2 * | 5/2008 | Palreddy et al. .............. 600/516 |
| 7,613,514 B2 | 11/2009 | Fogoros et al. |
| 7,979,124 B2 | 7/2011 | Meyer et al. |
| 2007/0219593 A1 | 9/2007 | Yonce et al. |
| 2010/0191132 A1 | 7/2010 | Jackson |
| 2011/0098768 A1 | 4/2011 | Arcit-Krishnamurthy et al. |

* cited by examiner

*Primary Examiner* — Brian T Gedeon
(74) *Attorney, Agent, or Firm* — Schwegman Lundberg & Woessner, P.A.

(57) ABSTRACT

A system senses a cardiac signal for diagnostic and/or therapy control purposes using a first set of electrodes and switches to a different second set of electrodes for recognizing cardiac events in the cardiac signal. In various embodiments, the cardiac signal sensed using the second set of electrodes is compared to the cardiac signal sensed using the first set of electrodes, and the cardiac events in the cardiac signal are each recognized using an outcome of the comparison.

10 Claims, 11 Drawing Sheets

METHOD AND APPARATUS FOR RECOGNIZING SENSED CARDIAC EVENTS USING DIFFERENT ELECTRODE CONFIGURATIONS

CLAIM OF PRIORITY

This application claims the benefit of priority under 35 U.S.C. §119(e) of Li et al., U.S. Provisional Patent Application Ser. No. 61/615,444, entitled "METHOD AND APPARATUS FOR RECOGNIZING SENSED CARDIAC EVENTS USING DIFFERENT ELECTRODE CONFIGURATIONS", filed on Mar. 26, 2012, which is herein incorporated by reference in its entirety.

TECHNICAL FIELD

This document relates generally to cardiac rhythm management systems and particularly to a sensing and detection system and related methods that recognize cardiac events by comparing signals sensed using different electrode configurations.

BACKGROUND

The heart is the center of a person's circulatory system. The left portions of the heart, including the left atrium (LA) and left ventricle (LV), draw oxygenated blood from the lungs and pump it to the organs of the body to provide the organs with their metabolic needs for oxygen. The right portions of the heart, including the right atrium (RA) and right ventricle (RV), draw deoxygenated blood from the body organs and pump it to the lungs where the blood gets oxygenated. These mechanical pumping functions are accomplished by contractions of the heart. In a normal heart, the sinoatrial (SA) node, the heart's natural pacemaker, generates electrical impulses, called action potentials, that propagate through an electrical conduction system to various regions of the heart to cause the muscular tissues of these regions to depolarize and contract. The electrical conduction system includes, in the order by which the electrical impulses travel in a normal heart, internodal pathways between the SA node and the atrioventricular (AV) node, the AV node, the His bundle, and the Purkinje system including the right bundle branch (RBB, which conducts the electrical impulses to the RV) and the left bundle branch (LBB, which conducts the electrical impulses to the LV). More generally, the electrical impulses travel through an AV conduction pathway to cause the atria, and then the ventricles, to contract.

Cardiac arrhythmias occur, for example, when the SA node fails to generate the electrical impulses at a normal sinus rate, when a portion of the electrical conduction system is partially or completely blocked, when a pathological conduction loop is formed in the heart, and/or when a pathologically formed electrical focus generates electrical impulses from the ventricles. Heart failure occurs when the myocardium (heart muscles) deteriorates to a degree that significantly impairs the heart's mechanical pumping functions. Electrical signals such as intracardiac electrograms sensed from the heart are used to monitor such conditions. Pacing and cardioversion/defibrillation therapies are applied to treat arrhythmias and heart failure by delivering electrical pulses to the heart. Accuracy in diagnosing cardiac conditions using a device and efficacy of many pacing and cardioversion/defibrillation therapies depend on the understanding of various cardiac events in the sensed electrical signals. Therefore, there is a need for providing accurate detection and recognition of these cardiac events.

SUMMARY

A system senses a cardiac signal for diagnostic and/or therapy control purposes using a first set of electrodes and temporarily switches to a different second set of electrodes for recognizing cardiac events in the cardiac signal. In various embodiments, the cardiac signal sensed using the second set of electrodes is compared to the cardiac signal sensed using the first set of electrodes, and the cardiac events in the cardiac signal are each recognized using an outcome of the comparison.

In one embodiment, a system is configured to be connected to a plurality of electrodes coupled to a heart to sense a cardiac signal from the heart. The system can include a sensing circuit, an electrode interface circuit, and a control circuit. The sensing circuit senses a cardiac signal indicative of cardiac events. The electrode interface circuit programmably connects the sensing circuit to a set of sensing electrodes selected from the plurality of electrodes according to a sensing configuration specifying the set of sensing electrodes. The control circuit can include an electrode configuration controller, an event detector, and an event recognition module. The electrode configuration controller sets the sensing configuration to a first sensing configuration during a first sensing period and sets a second sensing configuration during a second sensing period. The event detector detects first events of the cardiac events using the cardiac signal sensed during the first sensing period and detects second events of the cardiac events using the cardiac signal sensed during the second sensing period. The event recognition module recognizes one or more events of the first events each by origin using one or more events of the second events.

In one embodiment, a method of cardiac sensing is provided. A sensing circuit can be connected to a set of sensing electrodes selected from a plurality of electrodes according to a sensing configuration specifying the set of sensing electrodes. A cardiac signal indicative of cardiac events is sensed using the sensing circuit and the set of sensing electrodes. The sensing configuration is set to a first sensing configuration during a first sensing period and a second sensing configuration during a second sensing period. First events of the cardiac events are detected using the cardiac signal sensed during the first sensing period, and second events of the cardiac events are detected using the cardiac signal sensed during the second sensing period. One or more events of the first events are each recognized by origin using one or more events of the second events.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
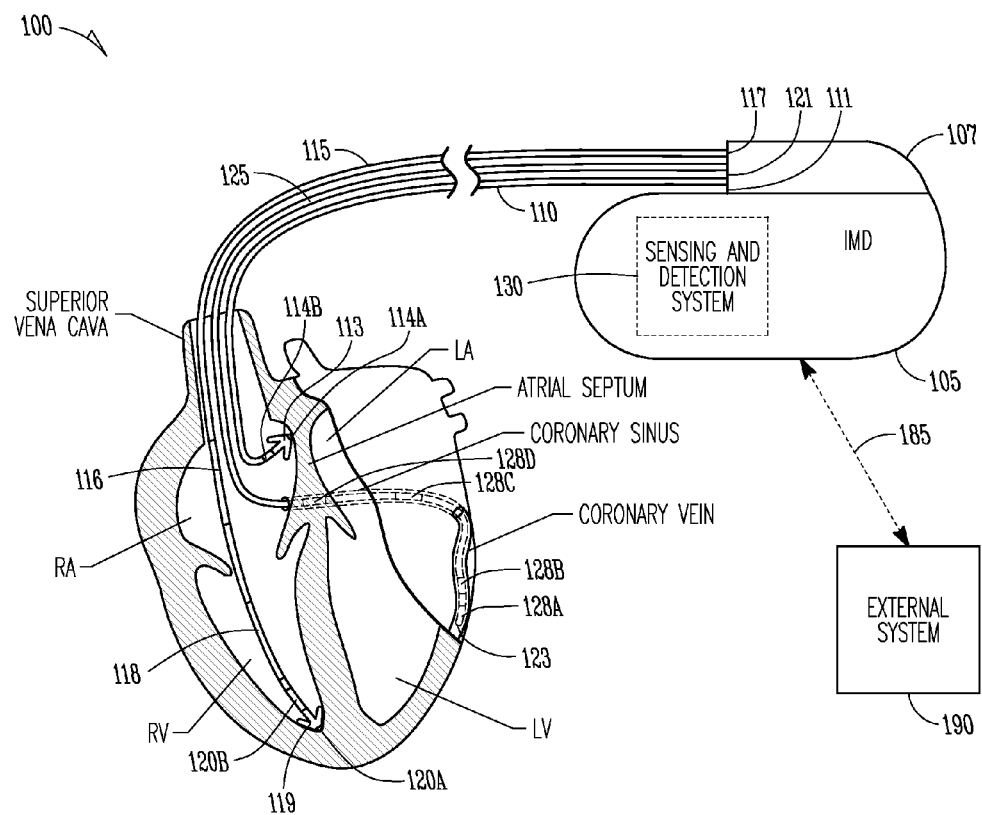
FIG. 1 is an illustration of an embodiment of a cardiac rhythm management (CRM) system and portions of an environment in which the system operates.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their legal equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this documents and those documents so incorporated by reference, the usage in the incorporated reference(s) should be considered supplementary to that of this document; for irreconcilable inconsistencies, the usage in this document controls.

It should be noted that references to "an", "one", or "various" embodiments in this disclosure are not necessarily to the same embodiment, and such references contemplate more than one embodiment.

This document discusses, among other things, a cardiac sensing and detection system and method for sensing a cardiac signal including multiple cardiac events in each cardiac cycle and recognizing each of the cardiac events by its origin. Accurate recognition of cardiac events in sensed electrograms is useful for proper diagnosis of a patient's cardiac conditions and proper control of cardiac therapies delivered to the patient. For example, in a cardiac resynchronization therapy (CRT) device with left ventricular (LV) sensing and pacing, one or more sensing electrodes in an LV lead may pick up signals originated from the LV as well as far-field signals originated from heart chambers other than the LV. Inappropriate sensing occurs when such far-field signals are recognized by the device as LV events. Properties of the LV electrogram sensed by the one or more sensing electrodes in the LV lead may be related to sensing vector configuration (electrode selection and arrangement) and may also depend on the location of each electrode (e.g., whether the electrode is near the coronary sinus or the atrioventricular groove). The far-field signals tend to be particularly significant when proximal electrodes (e.g., electrodes placed near the coronary sinus) are used for sensing in a multipolar LV lead. The present system senses a cardiac signal for diagnostic and/or therapy control purposes using a first sensing configuration (i.e., a first set of electrodes) and temporarily switches to a different second sensing configuration (i.e., a second set of electrodes) for the purpose of recognizing each cardiac event detected from the cardiac signal. In various embodiments, the cardiac signal sensed with the second sensing configuration is compared to the cardiac signal sensed with the first sensing configuration, and the cardiac events in the cardiac signal are each recognized using its known characteristics or detectability when being sensed with each of the sensing configurations.

While LV electrogram is discussed in this document as a specific example, the present system and method are applicable for event recognition from cardiac or other physiological signals sensed using any sensing electrode configurations. While application in an implantable medical device is discussed in this document as a specific example, the present system and method for event recognition from cardiac or other physiological signals are applicable with any system that have access to the target sensing site(s). For example, the present system and method may be implemented in an external pacemaker or pacing system analyzer that are electrically connected to intracardiac electrodes during implantation of an implantable cardiac device.

FIG. 1 is an illustration of an embodiment of a cardiac rhythm management (CRM) system 100 and portions of an environment in which system 100 operates. CRM system 100 includes an implantable medical device (IMD) 105 that is electrically coupled to a heart through implantable leads 110, 115, and 125. An external system 190 communicates with IMD 105 via a telemetry link 185.

IMD 105 includes a hermetically sealed can housing an electronic circuit that senses physiological signals and delivers therapeutic electrical pulses. In some examples, the hermetically sealed can also functions as an electrode (referred to as "the can electrode" hereinafter) for sensing and/or pulse delivery purposes. As shown in FIG. 1, IMD 105 can include a sensing and detection system 130 that senses cardiac signals from the heart and detects various cardiac events, such as depolarizations in each heart chamber, from the sensed cardiac signals. When multiple cardiac events are detected during a cardiac cycle from a cardiac signal, sensing and detection system 130 provides for recognition of each of the detected cardiac events by its origin. In one embodiment, IMD 105 can include a pacemaker that delivers cardiac pacing therapies. In another embodiment, IMD 105 can include a cardioverter/defibrillator that delivers cardioversion/defibrillation therapies. In yet another embodiment, IMD 105 can include a pacemaker and a cardioverter/defibrillator that delivers pacing and cardioversion/defibrillation therapies. IMD 105 can be configured to control the delivery of the cardiac pacing and/or cardioversion/defibrillation therapies using the cardiac signals sensed and the events detected and recognized by sensing and detection system 130. In various embodiments, IMD 105 includes one or more monitoring devices and therapeutic devices such as the pacemaker, the cardioverter/defibrillator, a neurostimulator, a drug delivery device, and a biological therapy device. In some cases, the pacemaker can provide bradycardia pacing, CRT, or both.

Lead 110 is a right atrial (RA) pacing lead that includes an elongate lead body having a proximal end 111 and a distal end 113. Proximal end 111 is coupled to a connector for connecting to IMD 105. Distal end 113 is configured for placement in the RA in or near the atrial septum. Lead 110 includes an RA tip electrode 114A, and an RA ring electrode 114B. RA electrodes 114A and 114B are incorporated into the lead body at distal end 113 for placement in or near the atrial septum, and are each electrically coupled to IMD 105 through a conductor extending within the lead body. RA tip electrode 114A, RA ring electrode 114B, and/or the can electrode allow for sensing an RA electrogram indicative of RA depolarizations and delivering RA pacing pulses.

Lead 115 is a right ventricular (RV) pacing-defibrillation lead that includes an elongate lead body having a proximal end 117 and a distal end 119. Proximal end 117 is coupled to a connector for connecting to IMD 105. Distal end 119 is configured for placement in the RV. Lead 115 includes a proximal defibrillation electrode 116, a distal defibrillation electrode 118, an RV tip electrode 120A, and an RV ring electrode 120B. Defibrillation electrode 116 is incorporated into the lead body in a location suitable for supraventricular placement in the RA and/or the superior vena cava. Defibrillation electrode 118 is incorporated into the lead body near distal end 119 for placement in the RV. RV electrodes 120A and 120B are incorporated into the lead body at distal end 119. Electrodes 116, 118, 120A, and 120B are each electrically coupled to IMD 105 through a conductor extending within the lead body. Proximal defibrillation electrode 116, distal defibrillation electrode 118, and/or the can electrode allow for delivery of cardioversion/defibrillation pulses to the heart. RV tip electrode 120A, RV ring electrode 120B, and/or the can of IMD 105 allow for sensing an RV electrogram indicative of RV depolarizations and delivering RV pacing pulses. In various embodiments, proximal defibrillation electrode 116 and/or distal defibrillation electrode 118 may also be used for sensing the RV electrogram.

Lead 125 is a left ventricular (LV) coronary pacing lead that includes an elongate lead body having a proximal end 121 and a distal end 123. Proximal end 121 is coupled to a connector for connecting to IMD 105. Distal end 123 is configured for placement in the coronary vein. Lead 125 includes an LV tip electrode 128A, a distal LV ring electrode 128B, and two proximal LV ring electrodes 128C and 128D. The distal portion of lead 125 is configured for placement in the coronary sinus and coronary vein such that LV electrodes 128A and 128B are placed in the coronary vein, and LV electrodes 128C and 128D are placed in or near the coronary sinus. LV electrodes 128A and 128B are incorporated into the lead body at distal end 123 and are each electrically coupled to IMD 105 through a conductor extending within the lead body. LV tip electrode 128A, distal LV ring electrode 128B, proximal LV ring electrode 128C, proximal LV ring electrode 128D, and/or the can electrode allow for sensing an LV electrogram indicative of LV depolarizations and delivering LV pacing pulses.

Electrodes from different leads may also be used to sense an electrogram or deliver pacing or cardioversion/defibrillation pulses. For example, an electrogram may be sensed using an electrode selected from RV electrode 116, 118, and 120A-B and another electrode selected from LV electrode 128A-D. The lead configuration including RA lead 110, RV lead 115, and LV lead 125 is illustrated in FIG. 1 by way of example and not by way of restriction. Other lead configurations may be used, depending on monitoring and therapeutic requirements. For example, additional leads may be used to provide access to additional cardiac regions, and leads 110, 115, and 125 may each include more or fewer electrodes along the lead body at, near, and/or distant from the distal end, depending on specified monitoring and therapeutic needs.

External system 190 can be configured to provide programming of IMD 105 and to receive signals acquired by IMD 105. In one embodiment, telemetry link 185 is an inductive telemetry link. In another embodiment, telemetry link 185 is a far-field radio-frequency telemetry link. However, it is contemplated that any suitable telemetry link may be used, as desired. Telemetry link 185 can provide for data transmission from IMD 105 to external system 190. This may include, for example, transmitting real-time physiological data acquired by IMD 105, extracting physiological data acquired by and stored in IMD 105, extracting therapy history data stored in IMD 105, and extracting data indicating an operational status of IMD 105 (e.g., battery status and lead impedance). Telemetry link 185 can also provide for data transmission from external system 190 to IMD 105. This may include, for example, programming IMD 105 to acquire physiological data, programming IMD 105 to perform at least one self-diagnostic test (such as for a device operational status), programming IMD 105 to run a signal analysis algorithm (such as an algorithm implementing the tachyarrhythmia detection method discussed in this document), and programming IMD 105 to deliver pacing and/or cardioversion/defibrillation therapies.

Figure 2:
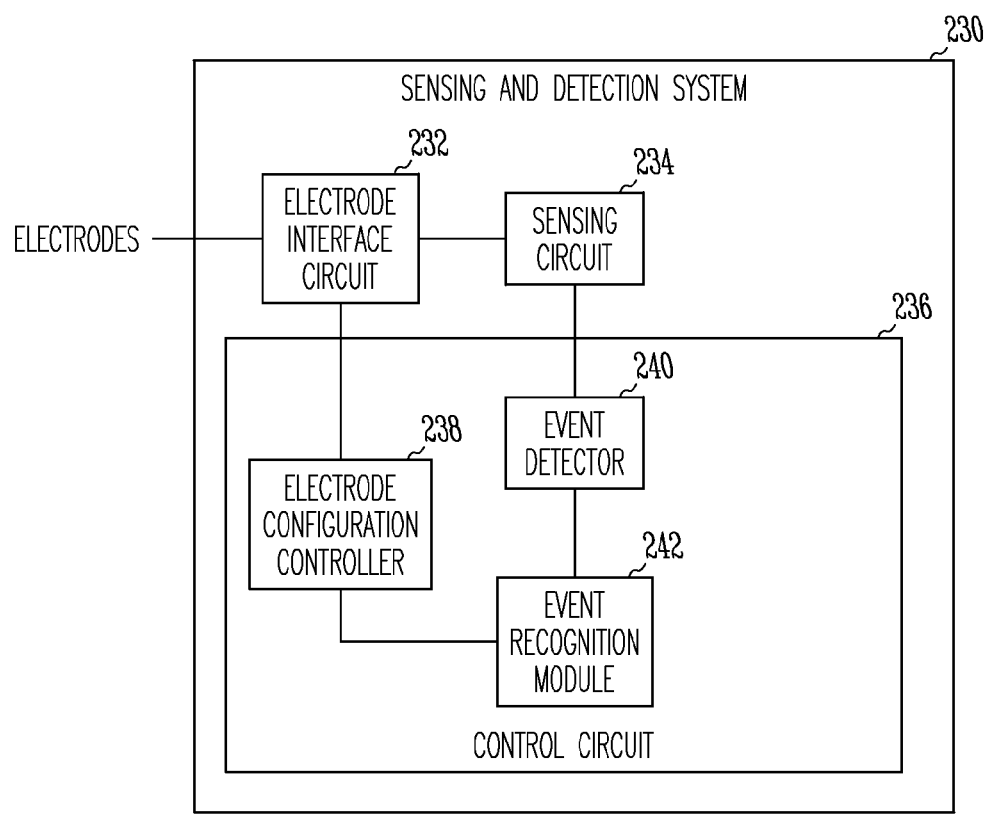
FIG. 2 is a block diagram illustrating an embodiment of a sensing and detection system.
Figure 3:
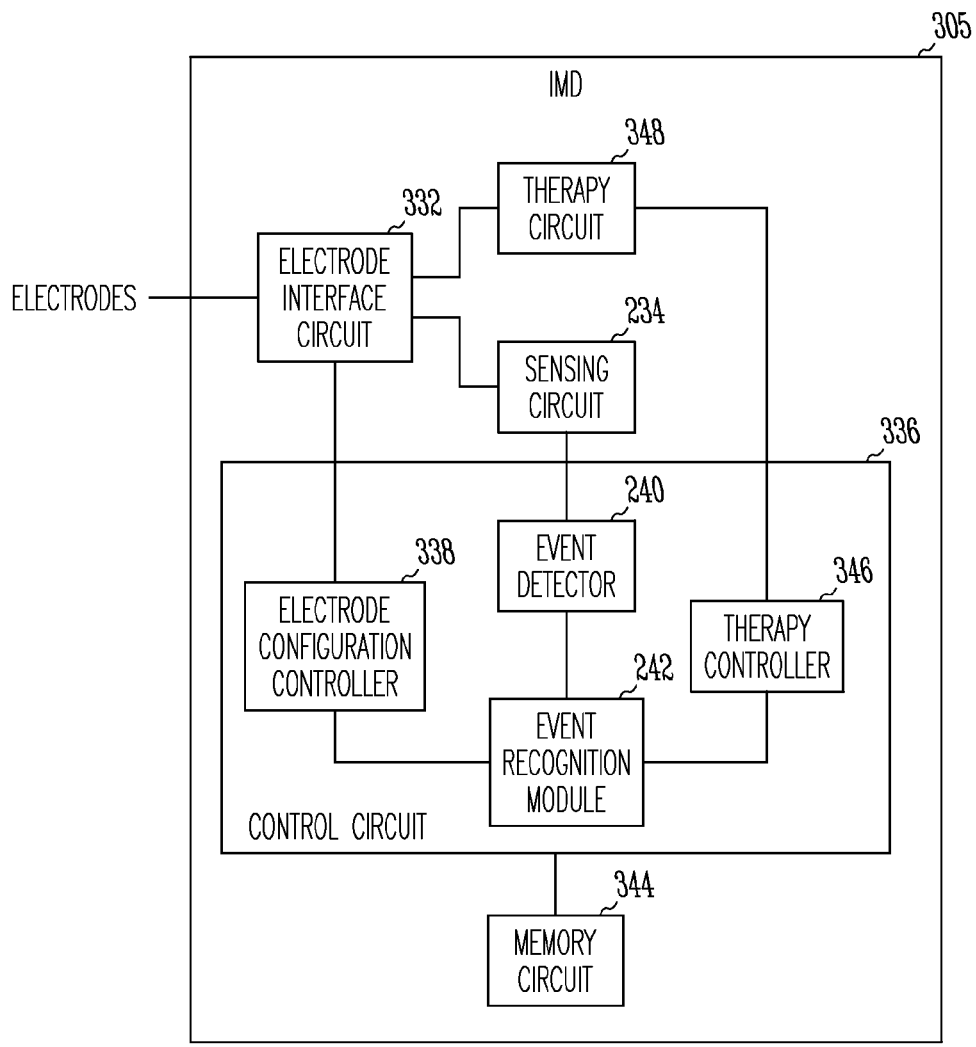
FIG. 3 is a block diagram illustrating an embodiment of portions of circuitry of an implantable medical device including the sensing and detection system.

The circuitry of CRM system 100 may be implemented using hardware, software, or a combination of hardware and software. In various embodiments, each element of IMD 105 as illustrated in FIGS. 2 and 3, including its various embodiments, may be implemented using an application-specific circuit constructed to perform one or more particular functions or a general-purpose circuit programmed to perform such function(s). Such a general-purpose circuit includes, but is not limited to, a microprocessor or portions thereof, a microcontroller or portions thereof, and a programmable logic circuit or portions thereof. For example, a "detector" includes, among other things, an electronic detection circuit constructed to perform the only function of detecting a specified type of events or a portion of a general-purpose circuit driven by a code instructing that portion of the general-purpose circuit to perform the detection.

FIG. 2 is a block diagram illustrating an embodiment of a sensing and detection system 230. System 230 can represent an embodiment of system 130 shown in FIG. 1 and includes a sensing circuit 234, an electrode interface circuit 232, and a control circuit 236.

Sensing circuit 234 senses a cardiac signal indicative of cardiac events. Electrode interface circuit 232 programmably connects sensing circuit 234 to a set of sensing electrodes selected from a plurality of electrodes according to a sensing configuration specifying the set of sensing electrodes. Examples of the sensing electrodes include, but are not limited to, electrodes 114A-B, 116, 118, 120A-B, and 128A-D. Control circuit 236 includes an electrode configuration controller 238, an event detector 240, and an event recognition module 242. Electrode configuration controller 238 sets the sensing configuration to a first sensing configuration during a first sensing period and a second sensing configuration during a second sensing period. Event detector 240 detects first events of the cardiac events using the cardiac signal sensed during the first sensing period and second events of the cardiac events using the cardiac signal sensed during the second sensing period. Event recognition module 242 recognizes one or more events of the first events each by origin using one or more events of the second events.

In various embodiments, the first sensing period is the period during which the cardiac signal is sensed for patient monitoring and/or therapy control purposes, and the second sensing period is a temporary period during which the cardiac signal is sensed for the recognition of cardiac events detected from the cardiac signal sensed during the first sensing period. Accordingly, the first sensing configuration can be the sensing configuration used for sensing the cardiac signal for patient monitoring and/or therapy control purposes, and the second sensing configuration can be a temporary sensing configuration used for sensing the cardiac signal for the recognition of cardiac events detected from the cardiac signal sensed using the first sensing configuration.

In one embodiment, control circuit 236 includes portions of a processor circuit, such as a microprocessor, a microcontroller, or a custom integrated circuit, that are programmed to control the sensing, event detection, and event recognition functions discussed in this document. Electrode configuration controller 238, event detector 240, and event recognition module 242 are each a portion of such a processor circuit programmed to perform the sensing configuration control, event detection, and event recognition functions, respectively.

FIG. 3 is a block diagram illustrating an embodiment of portions of circuitry of an IMD 305. IMD 305 can represent an embodiment of IMD 105 shown in FIG. 1 and includes sensing circuit 234, a therapy circuit 348, an electrode interface circuit 332, a control circuit 336, and a memory circuit 344.

Sensing circuit 234 senses the cardiac signal indicative of cardiac events. Electrode interface circuit 332 performs the function of electrode interface circuit 232 and, in some cases, can programmably connect therapy circuit 348 to a set of therapy electrodes selected from a plurality of electrodes. Examples of the sensing and/or therapy electrodes include, but are not limited to, electrodes 114A-B, 116, 118, 120A-B, and 128A-D. Therapy circuit 348 delivers one or more therapies to the heart. Examples of the one or more therapies include cardiac pacing therapy (including cardiac resynchronization therapy), cardioversion/defibrillation therapy, neurostimulation therapy, drug therapy, and biological therapy.

Control circuit 336 can include an electrode configuration controller 338, event detector 240, event recognition module 242, and a therapy controller 346. Electrode configuration controller 338 can control the connections between therapy circuit 348 and the set of therapy electrodes, and set the sensing configuration to the first sensing configuration during the first sensing period and the second sensing configuration during the second sensing period. Event detector 240 can detect first events of the cardiac events using the cardiac signal sensed during the first sensing period and second events of the cardiac events using the cardiac signal sensed during the second sensing period. Event recognition module 242 can recognize one or more events of the first events each by origin using one or more events of the second events. Therapy controller 346 can control the delivery of the one or more therapies from therapy circuit 348 using the cardiac signal sensed during the first sensing period. In various embodiments, therapy controller 346 can control timing of the delivery of the one or more therapies from therapy circuit 348 using timing of each of the recognized first events.

Memory circuit 344 can be configured to store data such as physiological data acquired by IMD 105, including the sensed cardiac signal and the detected cardiac events, therapy history data, or data indicating an operational status of IMD 105. In various embodiments, control circuit 336 causes at least portions of the cardiac signal sensed during the first sensing period to be stored in memory circuit 344. In various embodiments, memory circuit 344 can also be configured to store pre-specified sensing configurations including the first and second sensing configurations as discussed in this document.

In one embodiment, electrode configuration controller 338 can adjust at least one of the first sensing configuration and the second sensing configuration using an outcome of the recognition of the one or more events of the first events. For example, if event recognition module 242 is unable to recognize one of the first events, electrode configuration controller 338 adjusts the first sensing configuration and/or the second sensing configuration until all the detected events are recognized and usable for patient monitoring and/or therapy control purposes. In one embodiment, electrode configuration controller 338 adjusts the first sensing configuration in response to at least one event of the first events being unrecognizable by event recognition module 242. In another embodiment, electrode configuration controller 338 adjusts the second sensing configuration in response to at least one event of the first events being unrecognizable by event recognition module 242.

In some embodiments, the electrode configuration controller 338 can be configured to set the first and second sensing configurations for sensing an LV electrogram using unipolar or bipolar sensing configurations. For example, in one embodiment, electrode configuration controller 338 sets the first sensing configuration for sensing an LV electrogram using a bipolar sensing configuration and sets the second sensing configuration for sensing an LV electrogram using a unipolar sensing configuration. In another embodiment, electrode configuration controller 338 sets the first sensing configuration for sensing an LV electrogram using a unipolar sensing configuration and sets the second sensing configuration for sensing an LV electrogram using a bipolar sensing configuration. In another embodiment, electrode configuration controller 338 sets the first sensing configuration for sensing an LV electrogram using a first bipolar sensing configuration and sets the second sensing configuration for sensing an LV electrogram using a second bipolar sensing configuration that is different from the first bipolar sensing configuration. Examples of various sensing configurations are further discussed below with reference to FIGS. 6-11.

In one embodiment, electrode configuration controller 338 can set the sensing configuration to the second sensing configuration in response to an unrecognized event of the first events being detected by event detector 242. The second sensing period is triggered and, in some cases, lasts only when it is needed for recognizing the cardiac events detected from the cardiac signal sensed for patient monitoring and/or therapy control purposes.

Control circuit 336 can include a processor circuit, such as a microprocessor, a microcontroller, a custom integrated circuit, or portions thereof, that are programmed to control the sensing, event detection, event recognition, and therapy control functions discussed in this disclosure. In some examples, electrode configuration controller 338, event detector 240, event recognition module 242, and therapy controller 346 are each a portion of such a processor circuit programmed to perform the sensing configuration control, event detection, event recognition and therapy control functions, respectively.

Figure 4:
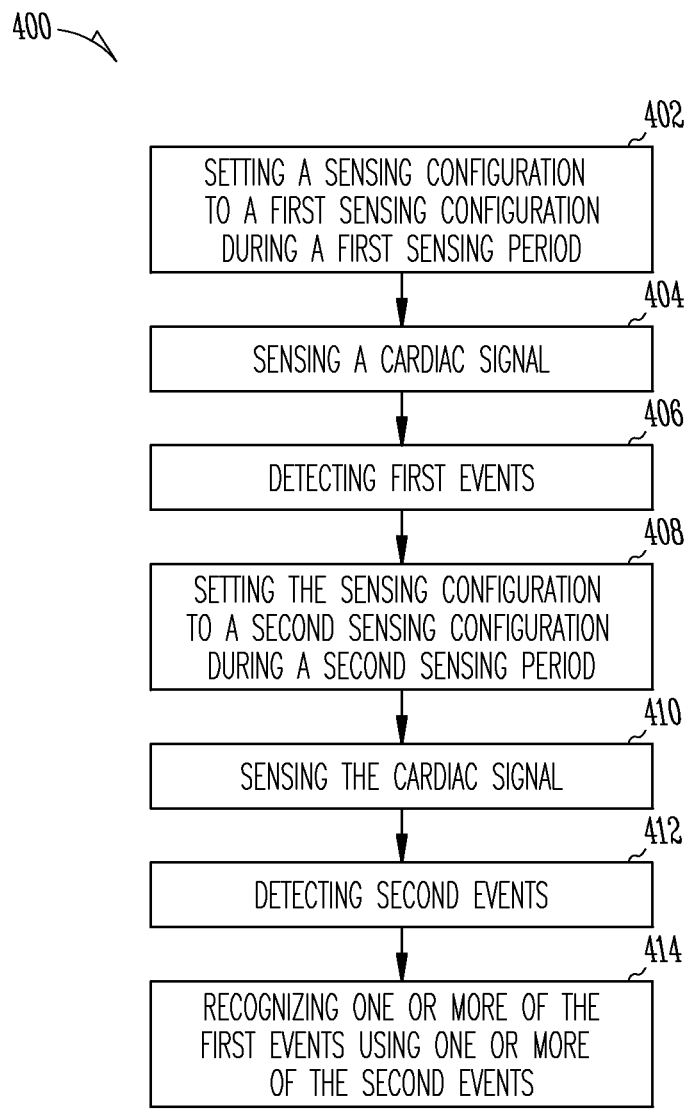
FIG. 4 is a flow chart illustrating an embodiment of a method for sensing and recognizing sensed cardiac events.

FIG. 4 is a flow chart illustrating an embodiment of a method 400 for sensing and recognizing sensed cardiac events. In one embodiment, IMD 105 and sensing and detection system 130, including their various embodiments discussed in this document, can be programmed to perform method 400.

At 402, a sensing configuration is set to a first sensing configuration during a first sensing period. This can include connecting a sensing circuit to a first set of sensing electrodes selected from a plurality of electrodes according to a first sensing configuration specifying the first set of sensing electrodes. At 404, a cardiac signal indicative of cardiac events is sensed during the first sensing period using the sensing circuit and the set of sensing electrodes. At 406, first events are detected using the cardiac signal sensed during the first sensing period. At 408, the sensing configuration is set to a second sensing configuration during a second sensing period. This can include connecting the sensing circuit to a second set of sensing electrodes selected from the plurality of electrodes according to the second sensing configuration specifying the second set of sensing electrodes. At 410, the cardiac signal is sensed during the second sensing period. At 412, second events are detected using the cardiac signal sensed during the second sensing period. At 414, one or more events of the first events are recognized using one or more events of the second events.

In various embodiments, a cardiac condition of a patient is monitored using the cardiac signal sensed during the first sensing period. Delivery of cardiac therapy to the patient can be controlled using the cardiac signal sensed during the first sensing period. In some examples, the second sensing period can be a temporary period initiated and timed for the recognition of the first events. For example, the second sensing period can be set to a time interval specified in seconds, such as a time interval between approximately 5 and 15 seconds. In one example, the second sensing period can be set to a time interval specified by a number of cardiac cycles (heart beats), such as a time interval covering approximately 5 and 20 cardiac cycles. Such specific time intervals, as examples, can be used to ensure reliable sensing when the sensing configuration is temporarily changed. In some instances, 15 seconds or 20 cardiac cycles for the second sensing period are sufficient to collect "good and reliable" sensing data for comparing to the sensing data acquired during the first sensing period; however, this is just one example. It is contemplated that shorter or longer time intervals, or other number of cardiac cycles can be used, as desired.

In one embodiment, IMD 105 buffers a sequence of electrogram sensed during the first sensing period and a sequence of electrogram sensed during the second sensing period (up to 15 seconds or 20 cardiac cycles), and determines representative sensed events within one cardiac cycle (using ensemble average for example) associated with each sensing configuration for the comparison between the cardiac signal sensed during the first sensing period and the cardiac signal sensed during the second sensing period.

In one embodiment, the first sensing configuration is specified for sensing an LV electrogram using a bipolar sensing configuration, and the second sensing configuration is specified for sensing an LV electrogram using a unipolar sensing configuration. One example of this is discussed below with reference to FIGS. 6 and 7.

In another embodiment, the first sensing configuration is specified for sensing an LV electrogram using a unipolar sensing configuration, and the second sensing configuration is specified for sensing an LV electrogram using a bipolar sensing configuration. One example of this is discussed below with reference to FIGS. 8 and 9.

In another example, the first sensing configuration is specified for sensing an LV electrogram using a first bipolar sensing configuration, and the second sensing configuration is specified for sensing an LV electrogram using a second bipolar sensing configuration that is different from the first bipolar sensing configuration. One example of this is discussed below with reference to FIGS. 10 and 11.

Figure 5:
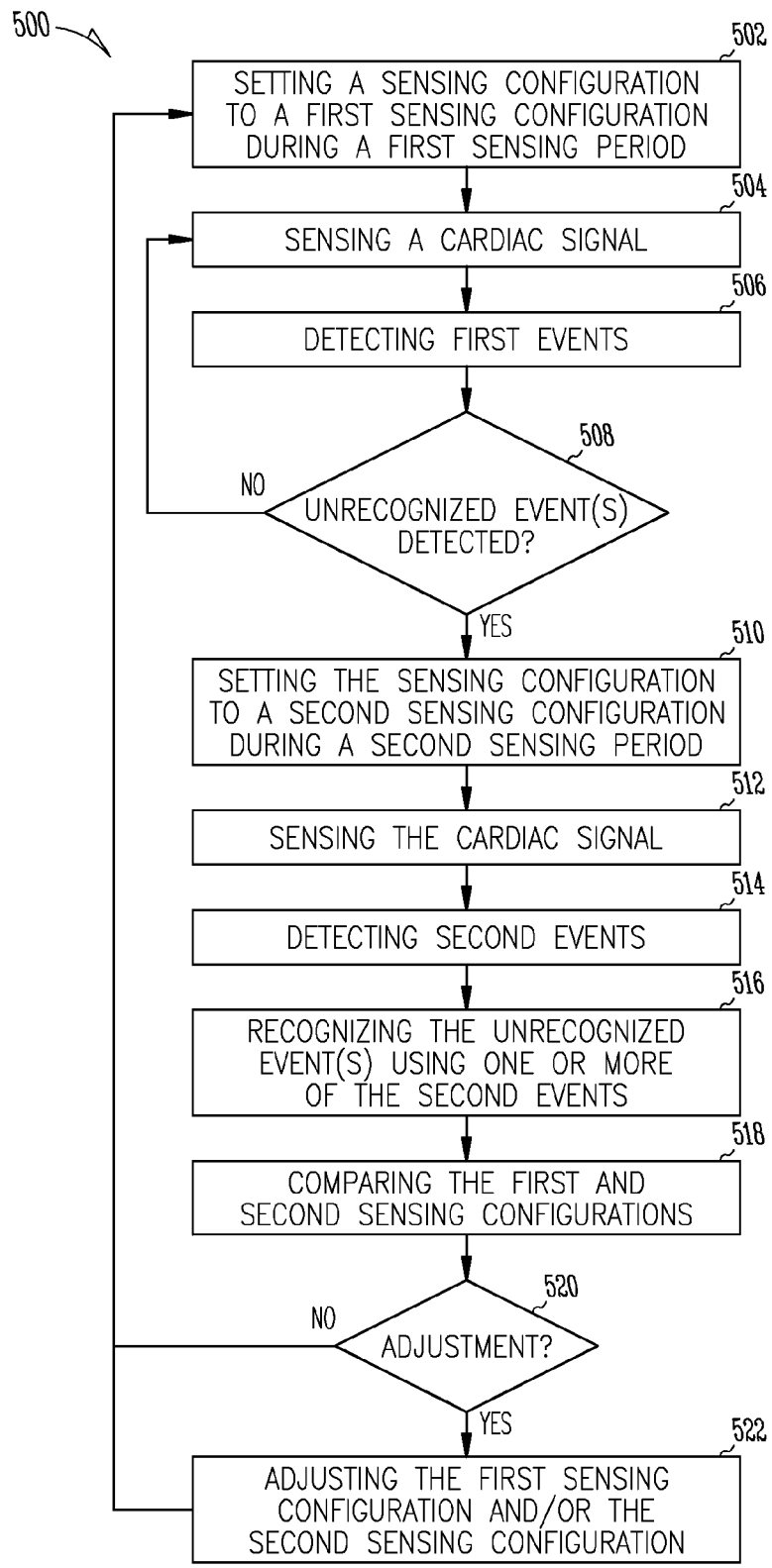
FIG. 5 is a flow chart illustrating another embodiment of a method for sensing and recognizing sensed cardiac events.

FIG. 5 is a flow chart illustrating an embodiment of a method 500 for sensing and recognizing sensed cardiac events. In one embodiment, IMD 105 and sensing and detection system 130, including their various embodiments discussed in this document, can be programmed to perform method 500.

At 502, the sensing configuration is set to the first sensing configuration during the first sensing period. At 504, the cardiac signal is sensed during the first sensing period. At 506, the first events are detected using the cardiac signal sensed during the first sensing period. The cardiac signal is continued to be sensed during the first sensing period if all of the first events are recognized at 508. At 510, the sensing configuration is set to the second sensing configuration during the second sensing period that is initiated in response to the first events including one or more unrecognized events at 508. In other words, the first sensing period is suspended, and the second sensing period is started, in response to detection of at least one unrecognized event of the first events.

At 512, the cardiac signal is sensed during the second sensing period. At 514, the second events are detected using the cardiac signal sensed during the second sensing period. At 516, the unrecognized one or more events of the first events are recognized using one or more events of the second events.

At 518, the first and second sensing configurations are compared to determine whether the first sensing configuration and/or the second sensing configuration should be adjusted. The sensing configuration is reset to the unadjusted first sensing configuration if such adjustment is determined to be unnecessary at 520. At 522, the first sensing configuration and/or the second sensing configuration are adjusted in response to the adjustment being determined to be unnecessary at 520. The adjustment becomes necessary, for example, when at least one event of the first events is unrecognizable at 516. In one embodiment, a user such as a physician or other care provider is alerted for the need to adjust the sensing configuration and presented with options for the adjustment. The user subsequently specifies electrodes for a new first and/or second sensing configuration. This may take several iterations until all of the first events are recognized.

FIGS. 6-11 illustrate various examples of methods for recognizing and differentiating cardiac events from electrogram sensed from an LV lead such as lead 125. The cardiac events to be recognized and differentiated include intrinsic LA depolarization (referred to as LA sense, or LAS), intrinsic LV depolarization (referred to as LV sense, or LVS), and intrinsic RV depolarization (referred to as RV sense, or RVS). While the LV lead may be primarily used for sensing LVS, other events including RVS and LAS may also be present in the sensed LV electrogram, to an extent dependent on the LV sensing configuration. On the other hand, sensing and detections of all the LAS, LVS, and RVS may be useful in providing relative timing between these events, which indicates various cardiac conduction abnormalities. In one embodiment, IMD 105, particularly sensing and detection system 130, including their various embodiments discussed in this document, can be programmed to perform methods 600, 800, and/or 1000, which are discussed below.

Figure 6:
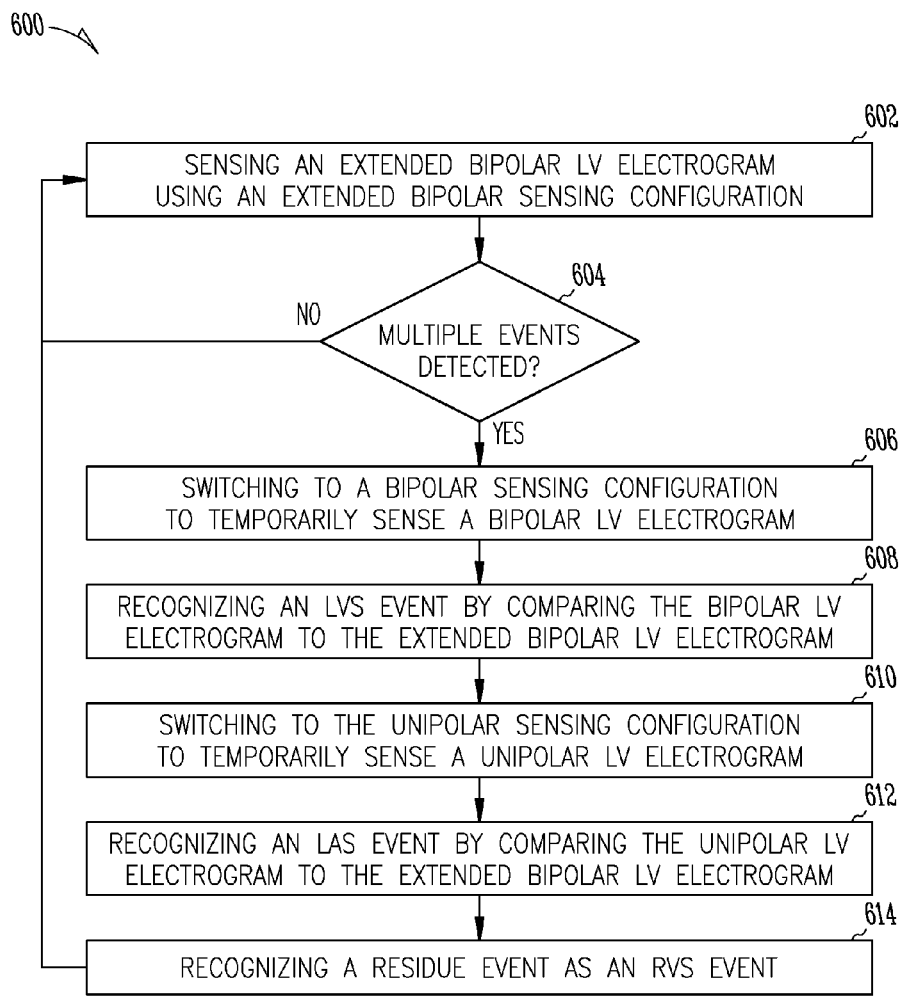
FIG. 6 is a flow chart illustrating an embodiment of a method for recognizing events sensed using an extended bipolar sensing configuration with a left ventricular (LV) lead.
Figure 7:
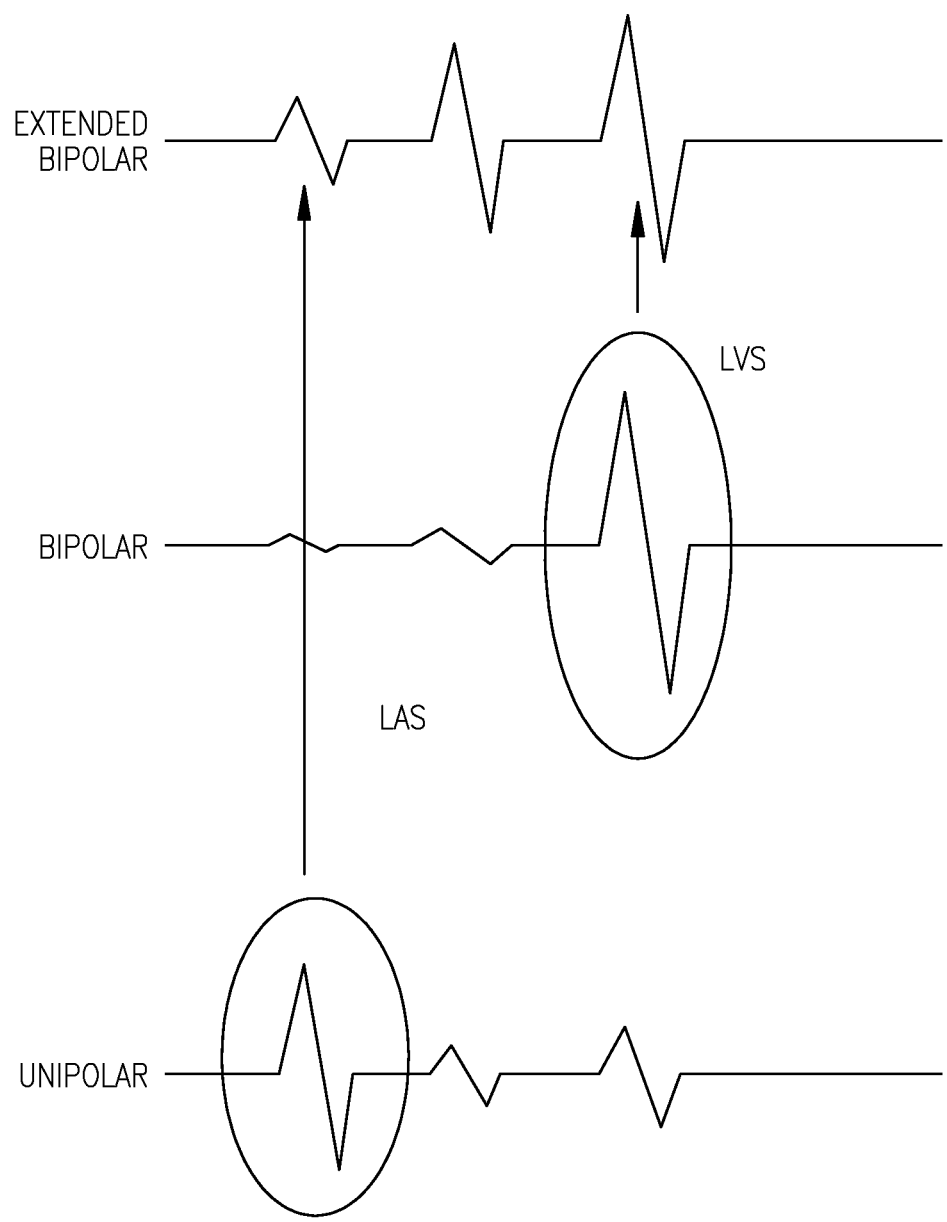
FIG. 7 is an illustration of electrograms including cardiac events sensed using the extended bipolar sensing configuration with the LV lead.

FIG. 6 is a flow chart illustrating an embodiment of method 600 for recognizing events sensed using an extended bipolar sensing configuration with an LV lead. FIG. 7 is an illustration of electrograms including cardiac events sensed using the extended bipolar sensing configuration with the LV lead as method 600 is performed. In method 600, the first sensing configuration is an "extended bipolar sensing configuration" which specifies an LV electrode and an RV electrode. In one example, the LV electrode is selected from electrodes 128A-D, and the RV electrode is selected from 118 and 120A-B. The second sensing configuration is a "bipolar sensing configuration" which specifies two LV electrodes. In one example, the two LV electrodes are selected from electrodes 128A-D. An additional second sensing configuration is a "unipolar sensing configuration" which specifies an LV electrode and the can electrode. In one example, the LV electrode is selected from electrodes 128A-D.

At 602, an extended bipolar LV electrogram is sensed using the extended bipolar sensing configuration. At 606, the sensing configuration is switched to the bipolar sensing configuration to temporarily sense a bipolar LV electrogram, in response to multiple events being detected from the extended bipolar LV electrogram at 604. At 608, an LVS event is recognized by comparing the bipolar LV electrogram to the extended bipolar LV electrogram. At 610, the sensing configuration is switched to the unipolar sensing configuration to temporarily sense a unipolar LV electrogram. At 612, an LAS event is recognized by comparing the unipolar LV electrogram to the extended bipolar LV electrogram. At 614, the residue event (a detected event remaining unrecognized after 608 and 612) is recognized as an RVS event.

In method 600, the bipolar sensing configuration is used to minimize or reduce the chance of picking up RVS and LAS during the LV electrogram sensing, and thus it is likely that only LVS is detected in the bipolar LV electrogram. The signal amplitude obtained from the bipolar LV electrogram is then compared to that of the extended bipolar LV electrogram. The event in the extended bipolar LV electrogram that is the closest in amplitude to the signal amplitude of the bipolar LV electrogram is the LVS (i.e., the "dominant depolarization"). The unipolar sensing configuration is used to minimize the RVS and LVS, and it is thus likely that only LAS is detected in the unipolar LV electrogram. The event in the extended bipolar LV electrogram that is the closest in amplitude to the signal amplitude of the unipolar LV electrogram is the LAS (i.e., the "dominant depolarization").

Figure 8:
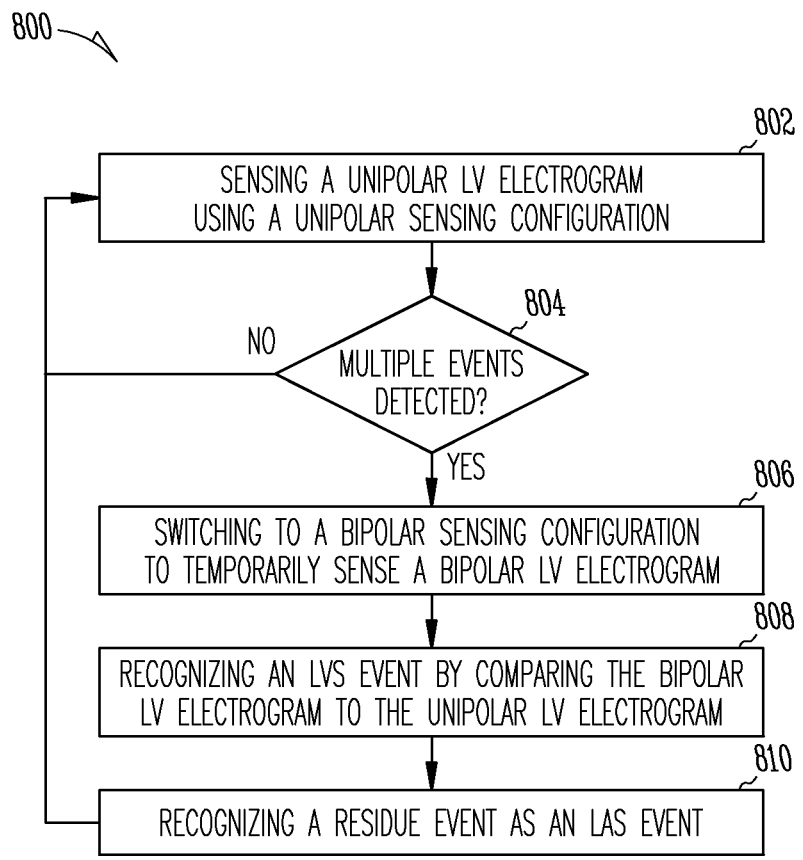
FIG. 8 is a flow chart illustrating an embodiment of a method for recognizing events sensed using a unipolar sensing configuration with an LV lead.
Figure 9:
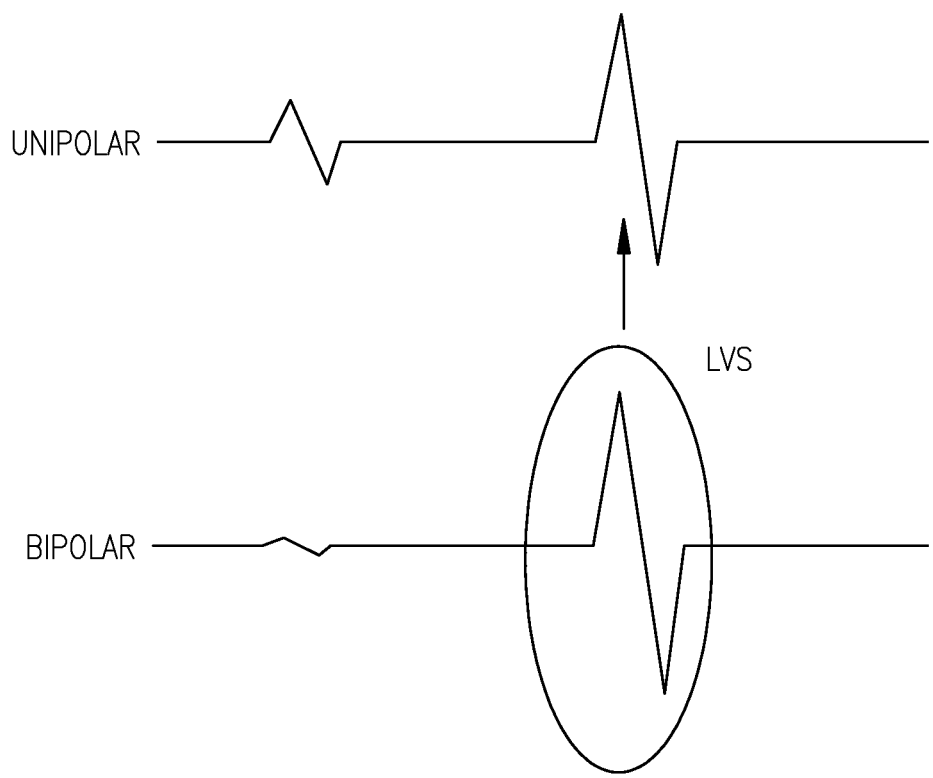
FIG. 9 is an illustration of electrograms including cardiac events sensed using the unipolar sensing configuration with the LV lead.

FIG. 8 is a flow chart illustrating an embodiment of method 800 for recognizing events sensed using a unipolar sensing configuration with an LV lead. FIG. 9 is an illustration of electrograms including cardiac events sensed using the unipolar sensing configuration with the LV lead as method 800 is performed. In method 800, the first sensing configuration is a "unipolar sensing configuration" which specifies an LV electrode and the can electrode. In one example, the LV electrode is selected from electrodes 128A-D. The second sensing configuration is a "bipolar sensing configuration" which specifies two LV electrodes. In one example, the two LV electrodes are selected from 128A-D.

At 802, a unipolar LV electrogram is sensed using the unipolar sensing configuration. At 806, the sensing configuration is switched to the bipolar sensing configuration to temporarily sense a bipolar LV electrogram, in response to multiple events being detected from the unipolar LV electrogram at 804. At 808, an LVS event is recognized by comparing the bipolar LV electrogram to the extended bipolar LV electrogram. At 810, the residue event (a detected event remaining unrecognized after 808) is recognized as an LAS event.

In method 800, the peak amplitude of each event detected from the bipolar LV electrogram can be measured and compared to the measured peak amplitude of the corresponding detected event in the unipolar LV electrogram. If the peak amplitude of an event in the bipolar LV electrogram is substantially smaller than the peak amplitude of the corresponding event in the unipolar LV electrogram, the event is recognized as an LAS event. For example, if the peak amplitude of the event in the bipolar LV electrogram is smaller than the peak amplitude of the corresponding event in the unipolar LV electrogram by a specified margin, the event is recognized as an LAS event. Otherwise, the event is recognized as an LVS event. In one example, the specified margin is a value programmable by the user.

Figure 10:
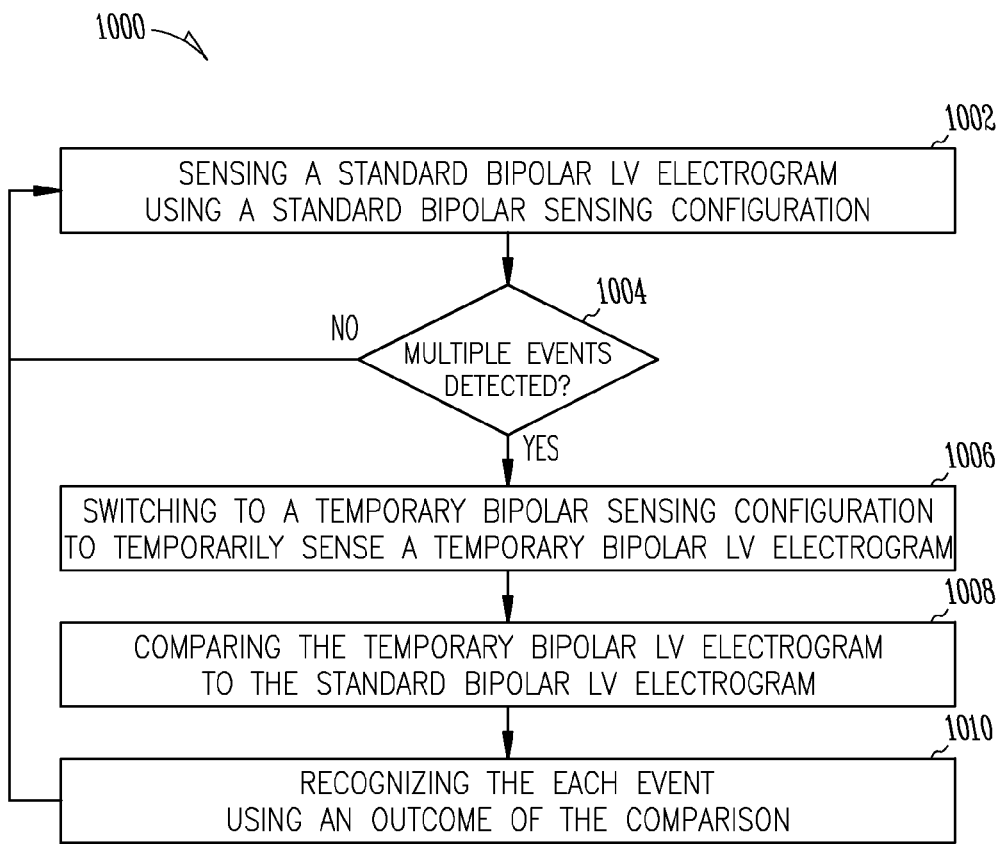
FIG. 10 is a flow chart illustrating another embodiment of a method for recognizing events sensed using a standard bipolar sensing configuration with an LV lead.
Figure 11:
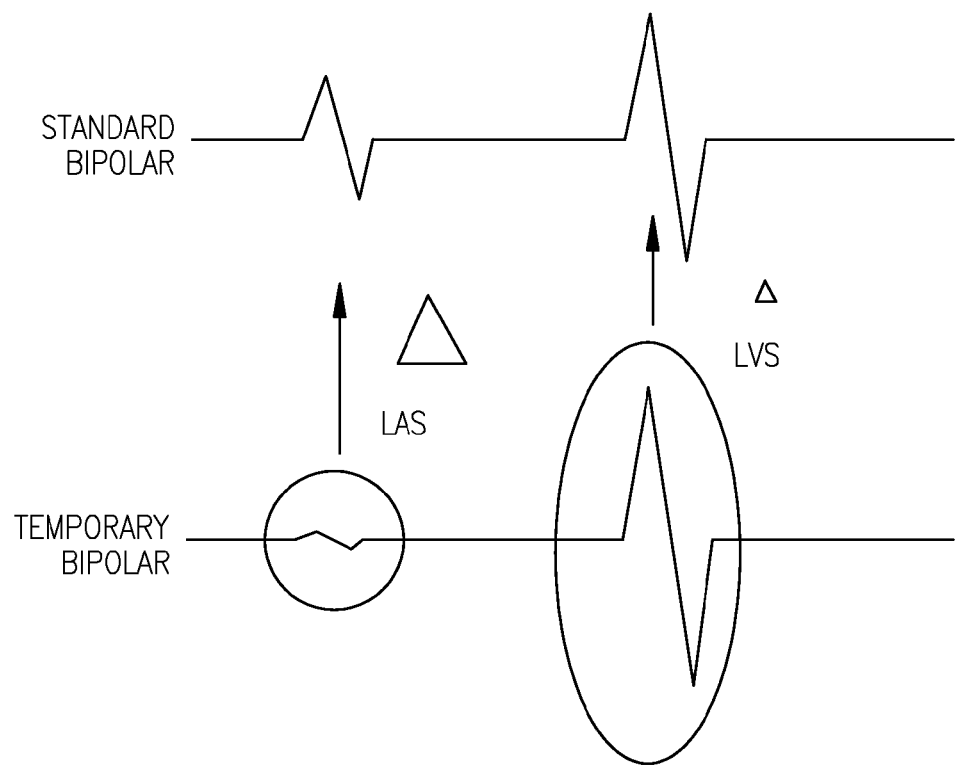
FIG. 11 is an illustration of electrograms including cardiac events sensed using the standard bipolar sensing configuration with the LV lead.

FIG. 10 is a flow chart illustrating another embodiment of method 1000 for recognizing events sensed using a standard bipolar sensing configuration with an LV lead. FIG. 11 is an illustration of electrograms including cardiac events sensed using the standard bipolar sensing configuration with the LV lead as method 1000 is performed. In method 1000, the first sensing configuration is a "standard bipolar sensing configuration" which specifies a first set of two LV electrodes. In one example, the two LV electrodes are selected from electrodes 128A-D. The second sensing configuration is a "temporary bipolar sensing configuration" which specifies a second set of two LV electrodes. In one example, the two LV electrodes are also selected from electrodes 128A-D. In one example, electrodes 128A-B are specified by the standard bipolar sensing configuration, and electrodes 128C-D are specified by the temporary bipolar sensing configuration.

At 1002, a standard bipolar LV electrogram is sensed using the standard bipolar sensing configuration. At 1006, the sensing configuration is switched to the temporary bipolar sensing configuration to temporarily sense a temporary bipolar LV electrogram, in response to multiple events being detected from the standard bipolar LV electrogram at 1004. At 1008, the temporary bipolar LV electrogram is compared to the standard bipolar LV electrogram. In one embodiment, the difference in amplitudes for each event of all events sensed in the temporary bipolar LV electrogram and the standard bipolar LV electrogram is computed. This difference in amplitudes is the difference between the amplitude of an event sensed in the temporary bipolar LV electrogram and the amplitude of the corresponding event sensed in the standard bipolar LV electrogram. At 1010, each event of the detected multiple events are recognized using an outcome of the comparison at 1008. In one embodiment, the computed difference in amplitudes is used to recognize each event of the detected multiple events.

In method 1000, the peak amplitude of each event detected from the temporary bipolar LV electrogram is measured and compared to the measured peak amplitude of the corresponding detected event in the standard bipolar LV electrogram. If the peak amplitude of an event in the temporary bipolar LV electrogram is substantially smaller than the peak amplitude of the corresponding event in the standard bipolar LV electrogram, the event is recognized as an LAS event. For example, if the peak amplitude of an event in the temporary bipolar LV electrogram is smaller than the peak amplitude of the corresponding event in the standard bipolar LV electrogram by a specified margin, the event is recognized as an LAS event. Otherwise, the event is recognized as an LVS event. In an example, the specified margin is a value programmable by the user.

Methods 600, 800, and 1000 are discussed above as examples and are not meant to be limiting in any manner. It is to be understood that different sensing configurations may be used as desired. For example, when the extended bipolar LV electrogram is sensed during the first sensing period, an electrogram including RAS and RVS may be sensed during the second sensing period. The RAS and RVS may be used as timing references for recognizing LAS and/or LVS based on the patient's activation sequence (which depends on the condition of the heart). In another example, when the unipolar LV electrogram is sensed during the first sensing period, an electrogram including RAS and RVS may also be sensed during the second sensing period. The RAS and RVS may be used as timing references for recognizing LAS and/or LVS based on the patient's activation sequence (e.g., the event preceding the RVS is an LAS, and the event following the RVS is an LVS).

In various embodiments, in addition to event recognition by comparing amplitudes of events as discussed above for methods 800 and 1000, morphological features of the events detected using different sensing configurations may also be compared for the event recognition. Examples of the morphological features include width of the depolarization and shape of the depolarization waveform.

In various embodiments, one or more second sensing configurations may be pre-specified or predetermined and stored for each first sensing configuration, and an event recognition process can be automatically triggered when the IMD suspects multiple events coexist in an LV electrogram, but this is not required. In various embodiments, in addition to the examples of sensing configurations discussed above, the present system and method may also be used with quadripolar or other multipolar leads with any number of electrodes.

Accurate detection of both LAS and LVS events may help improve CRT optimization including pacing timing and site optimization. Improved event sensing and recognition in a multiploar LV lead is critical to CRT optimization with various available sensing configurations, thereby taking advantage of the flexibility of the multiploar LV lead, such as a quadripolar/multipolar coronary sinus lead. LAS event recognition in the coronary sinus lead may also be useful in diagnosing and tracking atrial remodeling.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system adapted to be connected to a plurality of electrodes coupled to a heart, the system comprising:
   a sensing circuit configured to sense a cardiac signal indicative of cardiac events;
   an electrode interface circuit configured to programmably connect the sensing circuit to a set of sensing electrodes selected from the plurality of electrodes according to a sensing configuration specifying the set of sensing electrodes; and
   a control circuit coupled to the electrode interface circuit, the control circuit including:
      an electrode configuration controller configured to set the sensing configuration to a first sensing configuration during a first sensing period and set a second sensing configuration during a second sensing period;
      an event detector configured to detect first events of the cardiac events using the cardiac signal sensed during the first sensing period and detect second events of the cardiac events using the cardiac signal sensed during the second sensing period; and
      an event recognition module configured to recognize one or more events of the first events each by origin using one or more events of the second events.

2. The system of claim 1, further comprising a memory circuit, and wherein the control circuit is configured to store at least portions of the cardiac signal sensed during the first sensing period in the memory circuit.

3. The system of claim 2, further comprising a therapy circuit configured to deliver a therapy to the heart, and wherein the control circuit further comprises a therapy controller configured to control the delivery of the therapy using the cardiac signal sensed during the first sensing period.

4. The system of claim 3, wherein the electrode configuration controller is configured to adjust at least one of the first sensing configuration and the second sensing configuration using an outcome of the recognition of the one or more events of the first events.

5. The system of claim 4, wherein the electrode configuration controller is configured to adjust the first sensing configuration in response to at least one event of the first events being unrecognizable by the event recognition module.

6. The system of claim 4, wherein the electrode configuration controller is configured to adjust the second sensing configuration in response to at least one event of the first events being unrecognizable by the event recognition module.

7. The system of claim 1, wherein the electrode configuration controller is configured to set the first sensing configuration for sensing a left ventricular electrogram using a bipolar sensing configuration and set the second sensing configuration for sensing a left ventricular electrogram using a unipolar sensing configuration.

8. The system of claim 1, wherein the electrode configuration controller is configured to set the first sensing configuration for sensing a left ventricular electrogram using a unipolar sensing configuration and set the second sensing configuration for sensing a left ventricular electrogram using a bipolar sensing configuration.

9. The system of claim 1, wherein the electrode configuration controller is configured to set the first sensing configuration for sensing a left ventricular electrogram using a first bipolar sensing configuration and set the second sensing configuration for sensing a left ventricular electrogram using a second bipolar sensing configuration that is different from the first bipolar sensing configuration.

10. The system of claim 1, wherein the electrode configuration controller is configured to set the sensing configuration to the second sensing configuration in response to an unrecognized event of the first events being detected by the event detector.

* * * * *